United States Patent
Gooding et al.

(10) Patent No.: US 11,887,301 B2
(45) Date of Patent: Jan. 30, 2024

(54) SYSTEM AND METHOD FOR AUTOMATIC DELINEATION OF SCANNED IMAGES

(71) Applicants: Mirada Medical Limited, Oxford (GB); Mark John Gooding, Oxford (GB); Djamal Boukerroui, Oxford (GB); Daniel Balfour, Oxford (GB)

(72) Inventors: Mark John Gooding, Oxford (GB); Djamal Boukerroui, Oxford (GB); Daniel Balfour, Oxford (GB)

(73) Assignee: Mirada Medical Limited, Oxford (GB)

( * ) Notice: Subject to any disclaimer, the term of this patent is extended or adjusted under 35 U.S.C. 154(b) by 485 days.

(21) Appl. No.: 17/284,555

(22) PCT Filed: Oct. 2, 2019

(86) PCT No.: PCT/EP2019/076743
§ 371 (c)(1),
(2) Date: Apr. 12, 2021

(87) PCT Pub. No.: WO2020/078725
PCT Pub. Date: Apr. 23, 2020

(65) Prior Publication Data
US 2021/0319557 A1 Oct. 14, 2021

(30) Foreign Application Priority Data

Oct. 19, 2018 (GB) .................................. 1817049
Jul. 24, 2019 (GB) .................................. 1910573

(51) Int. Cl.
*G06T 7/00* (2017.01)
*G06N 20/00* (2019.01)
(Continued)

(52) U.S. Cl.
CPC ............. *G06T 7/0012* (2013.01); *G06N 3/04* (2013.01); *G06N 20/00* (2019.01); *G06T 3/0075* (2013.01);
(Continued)

(58) Field of Classification Search
CPC ..... G06T 7/0012; G06T 3/0075; G06T 3/608; G06N 20/00; G06N 3/04
See application file for complete search history.

(56) References Cited

U.S. PATENT DOCUMENTS 10,867,417 B2 * 12/2020 Han ........................ A61B 5/055
11,077,320 B1 * 8/2021 Hibbard ................ G16H 20/40
(Continued)

FOREIGN PATENT DOCUMENTS

WO 2018048507 A1 3/2018

OTHER PUBLICATIONS

American Association of Physicists in Medicine, Med. Phys. 43 (3), Mar. 2016, A. Mehranian et al., "Vision 20/20: Magnetic resonance imaging-guided attenuation correction in PET/MRI: Challenges, solutions and opportunities", pp. 1130-1155 XP012204972; See especially introduction, sections 2.B.1 & 2.B.2 and Figure 1.
(Continued)

*Primary Examiner* — David Bilodeau
(74) *Attorney, Agent, or Firm* — Optimus Patents US, LLC (57) ABSTRACT

A method and system for generating synthetic images for use in a database is described. The database is used for delineation of features in real images, the method comprising the steps of: providing a delineated image acquired using a first scanner, defining a model related to the generation of synthetic images using a second scanner, processing the delineated image using the model to generate a synthetic image, mapping contours to the synthetic image to form a
(Continued)

synthetic image-contour pair; repeating providing, defining and processing steps to generate a plurality of synthetic images and contour pairs for the database; using said database of synthetic images and contour pairs to optimise a contouring algorithm, where the optimised algorithm generates contours for the real images of the same type as the synthetic images; processing one or more further real images to contour and delineate features on the further real image using the algorithm.

15 Claims, 8 Drawing Sheets

(51) Int. Cl.
  *G06N 3/04* (2023.01)
  *G06T 3/00* (2006.01)
  *G06T 3/60* (2006.01)
(52) U.S. Cl.
  CPC .... *G06T 3/608* (2013.01); *G06T 2207/10081* (2013.01); *G06T 2207/10088* (2013.01); *G06T 2207/10132* (2013.01); *G06T 2207/20081* (2013.01); *G06T 2207/20084* (2013.01)

(56) References Cited

U.S. PATENT DOCUMENTS

| | | | |
|---|---|---|---|
| 2017/0072222 A1* | 3/2017 | Siversson | A61B 6/5247 |
| 2017/0337682 A1 | 11/2017 | Siemens | |
| 2020/0303062 A1* | 9/2020 | Tao | G06N 99/00 |
| 2021/0004957 A1* | 1/2021 | Aalamifar | G06T 7/10 |

OTHER PUBLICATIONS

A Parsa et al: "Influence of cone beam CT scanning parameters on grey value measurements at an implant site", Dento-Maxillo-Facial Radiology, vol. 42, No. 3, Mar. 1, 2013 (Mar. 1, 2013), p. 79884780, XP55654272, SE ISSN: 0250-832X, DOI: 10.1259/dmfr/79884780 the whole document.

* cited by examiner

SYSTEM AND METHOD FOR AUTOMATIC DELINEATION OF SCANNED IMAGES

FIELD OF INVENTION

This invention relates to the fields of imaging scans and image scan processing. In particular, the contouring of cone-beam computed tomography images for monitoring radiotherapy treatment by, for example, a radiation oncologist, or other health care professional.

BACKGROUND OF INVENTION

A variety of technologies can be used to provide image scans of human internal anatomy. These may be medical scans for monitoring medical treatment, or for observing changes in human anatomy—in response to medical treatment for example. Typical modern sources of medical images are ultrasound scans, Computed Tomography (CT) scans and Magnetic Resonance Imaging (MRI) scans.

Most medical imaging involves images of humans. However, images may also be obtained of non-human animals, particularly as part of medical research projects. Medical images need to be read, analysed and reviewed by specialists.

Medical images may include information about a wide variety of anatomical features, structures, spaces and distances. For example, an image may show various types of healthy tissue, such as bone and/or organs, within the body. An image may also show abnormal tissues, such as tumours, cysts, swollen glands or other lesions. The word 'tumour' should henceforth be construed to include other types of abnormal tissues.

It is often necessary to estimate the size and volume of anatomical structures that are shown in medical images. The size of healthy tissue may be determined in order, for example, to measure growth of the tissue in a particular subject.

These estimates may also serve, for example, to monitor the growth of abnormal tissue. Both the size of abnormal tissue, and the spacing between abnormal tissue and healthier tissue, may be of interest.

Here a 'structure' should be interpreted very broadly, and might include:
 (i) A single entity, such as an organ, bone or tumour.
 (ii) A group of essentially separate objects, such as ribs in a rib cage, or two separate tumours visible on one image.
 (iii) A gap bordered by two or more objects or edges, such as the spacing between a tumour and the surface of a body, or between a tumour and a nearby organ.

Henceforth, a 'structure' that may be measured on an image may in fact be a single entity, or even a spacing between two different entities.

One prior art example where measurements are necessary is in the reading of images from cancer patients. Measurements of the principal dimensions of any suspected tumours are typically required for diagnosis and staging of disease. These measurements are also required for assessing the efficacy of any administered treatment.

In other fields of medicine, it may be necessary to obtain estimates of:
 (i) The size or volume of normal anatomy, e.g. organs; or
 (ii) Distances or angles between anatomical structures.

Much existing medical practice was developed for non-digital 2-d images, such as X-Ray films. Radiologists may obtain measurements directly from the hard copy of the image, using callipers or a ruler.

However, medical images are increasingly obtained and manipulated in digital format. In digital Radiology, either 2-d ('2-d') or 3-d ('3-d') images may be available. If the original image was only 2-d, then a user views a 2-d representation of that image.

A 3-d image from a scan typically includes a large volume of data points. Henceforth, the word 'image' describes the collection of all these data points. Normally therefore an 'image' will mean a 3-d image, but some embodiments of the present invention are applicable to 2-d images, such as those often obtained from ultrasound scans.

A user will normally view only one individual 2 dimensional 'slice' through the 3-d image. An image slice from a 3-d image is simply a 2-d representation, consisting of those data points that lie on a particular 2-d plane through the 3-d image. A typical 3-d image, such as one from an MRI scan, will have a matrix of regularly spaced data points. As a non-limiting example, the MRI-scan may have data points whose centres are spaced by 1 millimetre in the x- and y-directions across any plane of the scan. Consecutive planes may, for example, be parallel and separated by 7 millimetres.

Although it is usual for data points to be in the plane of a viewed image slice, it is possible that the points only lie near to the plane of the slice, for example when an 'off-axis' viewing angle has been selected.

Figure 1:
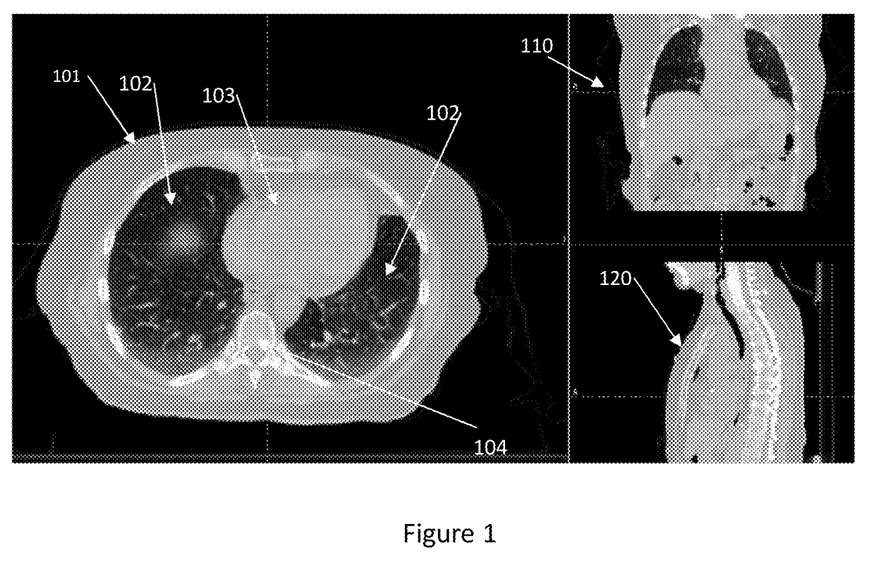
FIG. 1 shows an example of a 3D CT scan image.

Radiotherapy (RT) is a key method for treating cancer in which high energy radiation is directed at a tumour to destroy it by disrupting DNA replication. However, it is inevitable that surrounding healthy tissue is also irradiated during the process. It is therefore necessary to plan therapy with the aim to maximise the tumour's received dose while minimising the dose to healthy tissue. Teams of clinical experts spend a great deal of time developing treatment plans prior to their administration. In order to do so, a 3D Computed Tomography (3DCT) image of the patient is acquired. A typical 3DCT image is shown in FIG. 1.

When a radiation oncologist reaches the point of planning interventions in radiotherapy, they may use planning software to calculate a treatment plan. That plan typically maximises the radiation dose to be delivered to the target volume and tumour, while minimising the radiation dose to the surrounding healthy tissues, referred to in radiotherapy as organs-at-risk (OARs). Thus accurate delineation (target volumes+OARs) and targeting of patient anatomy is very important during treatment planning. This example serves to illustrate the value of any input that can be provided by the enhancement, analysis and interpretation of original CT and MR images.

Contouring

The process of delineating structures within an image is also known as 'contouring'. The term contouring may be used to indicate the process of delineation in either 2D or 3D, to define the boundary of an anatomical structure. Similarly, the term 'auto-contouring' may be used to indicate the process of producing a contour automatically, and this is discussed further in a separate section below.

Medical scan images of anatomical structures are typically approved by trained radiation oncologists, dosimetrists or radiographers for subsequent treatment planning. Approved images of anatomical structures may be referred to as 'gold-standard contours'. Gold-standard contours are therefore contours that have been curated and approved by expert clinicians as having high quality. Gold-standard contours are sometimes also termed 'ground-truth' contours. An 'atlas' comprises the pairing of an image and the gold-standard contours for that image. Gold-standard contours are often created in accordance with a given set of contouring guidelines. One such set of contouring guidelines is the 'RTOG' guidelines at: https://www.rtog.org/CoreLab/ContouringAtlases.aspx The atlases, each comprising gold-standard contours and a corresponding image, can be stored in a database, thereby providing a database of atlases. The atlases are then available for various uses with images that are obtained subsequently. Atlases in the database can act as an accumulated store of information, which may greatly improve the processing of subsequent, newly acquired images. Atlases are used to facilitate the contouring of newly acquired patient images, which typically are not images of the same patient as the image from which the atlas and its gold standard contours were derived.

Manual contouring of a medical scan image by a human operator is time consuming, and subject to variability in delineating the anatomical structures. Such variability is due to intra- and inter-operator variation, as well as protocol variations between different medical institutions, or different departments in one medical institution. In fact, different institutions, or even different groups within an institution, may have different contouring guidelines for OARs. Differences between contouring guidelines can exist because the different institutions may subsequently use different protocols for research evaluation or at the stage of planning subsequent treatment. For example, a protocol used at institution A may not be usable at institution B. Within the same institution, different protocols may also be employed, depending for example on the stage and location of a structure such as a tumour.

As a consequence, there may be variations in the gold-standard contours that are generated for a single medical scan image. These variations depend on factors such as the institution/department guidelines and protocols, the state of an organ in the image, and individual operators who process the images.

Thus, manual contouring represents one of the institutional bottlenecks in Radiotherapy planning. Furthermore, the variability in guidelines and protocols increases the required time for the quality assurance of manual contours.

Auto-Contouring

As discussed above, the process of contouring is time consuming and subject to inter-observer variation. Consequently, a number of methods have been proposed to automate, or partially automate this process. Auto-contouring methods aim, at least in part, to overcome the issues described above.

Auto-contouring methods may generate contours using different technologies. One example of such technologies involves the use of previously delineated cases. Another example of such technologies involves developing model-based approaches. The results of auto-contouring may still require manual editing to account for inaccuracies, and to make the results adhere to an institution or department's contouring guidelines, i.e. to provide a suitable input to subsequent protocols that are in use at that institution or department. In this case, the editing time for the results of auto-contouring can be significantly less than the time that would be required to manually delineate the entire image volume.

The term 'auto-contouring' is a collective description for various underlying approaches. The underlying technological approaches may actually differ widely between systems.

In generating an auto-contouring method, the organs within one or more example medical images, normally CT images, are carefully delineated by a clinical expert to generate gold-standard contours following specific contouring guidelines. This combination of a medical image and gold-standard structures is the 'atlas', that is used in Atlas-based auto-segmentation (ABAS).

In single ABAS, one 3DCT scan image of a previous already contoured case (known as an atlas) is aligned to the planning 3DCT scan image of the current patient using deformable image registration [1]. Following this, the contours from the atlas are then transferred or warped to the patient image using the alignment found by the deformable image registration. Where more than one atlas has been used, the process is referred to as multiple ABAS. In this approach, the registration and contour warping operations are repeated for several atlases, then the resulting warped contours on the patient image are fused into a consensus contour. However, a number of problems exist with this approach. First, the deformable image registration is subject to error, and will not accurately align the atlas to the patient scan image. Contour fusion from multiple atlases overcomes this to some extent by averaging out random errors in alignment between different atlases. However, errors still remain as a result of suboptimal image registration. Second, the image registration may not be able to overcome large anatomical differences between the atlas and the patient. Some implementations attempt to select the atlas, or atlases, that are most similar to the patient in order to overcome this. To successfully achieve a good result would require a very large database, even if the atlas selection process was optimal [2].

As a consequence of these limitations, ABAS is far from perfect. This has led to some to adopt machine learning (ML)-based approaches to automatically contour the 3DCT scan image [3]. In a ML contouring, a database of atlases are used to train a model which relates image appearance to contour location. The model can then be applied to a new patient 3DCT scan image to generate a contour for that patient. Given sufficient training data (3D CT image+Contours), this approach is capable of generating contours that are indistinguishable from those drawn manually [4]. Notice however that in contrast to an ABAS system where the set of Atlases are always needed to contour a new case, in a ML solution only the model is need.

Dose Fractionation and Treatment Delivery.

Generally, Radiation therapy is delivered in fractions, such that the entire planned treatment radiation dose may be split across many weeks. Each daily treatment is known as a fraction. 35 daily fractions of treatment are not uncommon. Dose fractionation maximizes the effect of radiation on cancer and minimizes the negative side effects on OARs. However, fractionation comes with the need of a daily repositioning of the patient on the treatment machine. In practice, this involves taking an image of the patient to perform an accurate patient positioning prior to treatment. This is known as Image-guided radiotherapy. However, the patient anatomy may have changed in response to earlier treatment, and therefore the present treatment plan may no longer be appropriate. It is desirable to detect and to quantify such change in the patient anatomy to trigger the clinical team to re-plan the patient. This can be achieved either by quantifying the change in anatomy, or more desirably, by the estimation of the radiation dose that will be delivered to the tumour and organs at each fraction of the treatment given the current plan [5].

Historically, image-guided radiotherapy employed radiographic films and electronical portal imaging devices to obtain 2D projection guidance images using the treatment beam itself. To obtain reliable 3D tumour localisation and tracking during treatment requires CT-based technologies, ideally with the imaging device as a part of the RT apparatus (the linac). This has proven challenging for conventional fanbeam 3DCT. However, the advancement of 2D flat panel imager devices led to the development of Cone-Beam CT (CBCT) as a lower-quality but practical alternative.

In CBCT, a 2D flat panel imager and X-ray source are affixed to the linac gantry. The gantry needs to only rotate once to obtain enough 2D projections to reconstruct a full 3D image. Additionally, the same hardware can be used in fluoroscopy mode for live tracking whilst the beam is on. However, CBCT projections suffer from increased scattered radiation and noise levels. This leads to poorer-quality reconstructed images which contain artefacts and unreliable measurements of attenuation, giving them a significantly different character to state-of-the-art 3DCT images [20].

Figure 2:
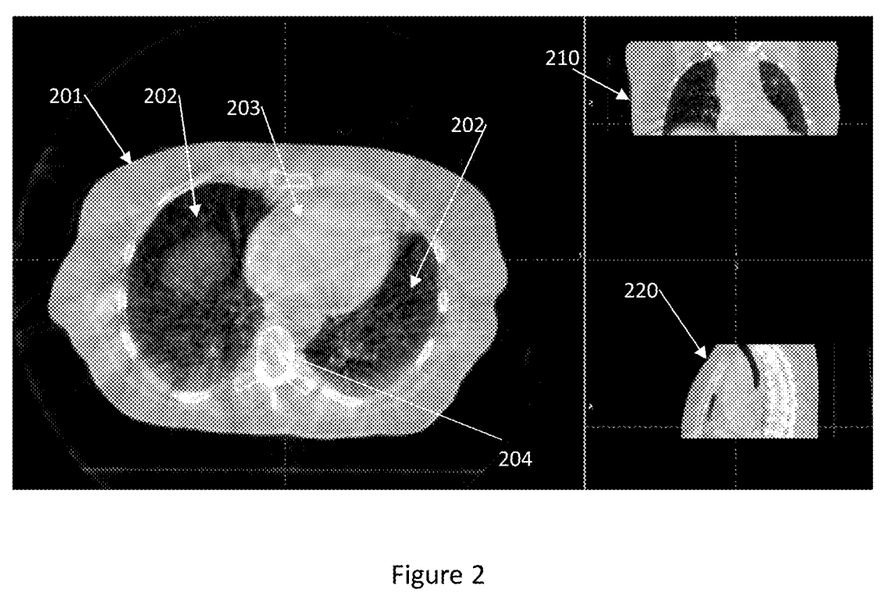
FIG. 2 shows an example of a CBCT scan image.

FIG. 1 shows examples of 3DCT scan images. As shown, 101 is an axial view of a subject where the lungs are shown at 102, the heart is shown at 103, and the spinal column at 104. 110 is the corresponding coronal view of the subject, and 120 is the corresponding sagittal view of the subject. FIG. 2 is a corresponding CBCT scan image of the same subject 201. Again, this image has cross-sectional view of the subject 201, face on view 210 and side view 220.

As can be seem from these images, the resolution of the CBCT scan image is not as sharp as the resolution in the comparable 3DCT scan image, and boundaries between features on the image are less well defined, for example in image 101 the boundary of the heart can be seen on the cross-sectional image, whereas this boundary is less well defined on the CBCT scan image.

Whether quantifying a change in patient anatomy or estimating the daily radiation dose to be provided to the patient, it is necessary to contour the CBCT scan image to identify the OARs and the tumour in the patient. However, manual contouring of the CBCT scan image to do these calculations is too laborious to be performed on a daily basis—and therefore it is not performed. Current state-of-the-art is to perform a deformable image registration between the patient's planning 3DCT scan image acquired at the start of the treatment and the daily CBCT scan image, and to use this registration to map the contours from the planning 3DCT scan image to the CBCT scan image (e.g. [6]). This follows a similar approach to ABAS as previously described, with the difference that the patient's own planning 3DCT scan image is being used as the atlas.

As with ABAS, this registration between the images is subject to errors [7]. However, there is only one atlas available as the method uses the patient's own contoured 3DCT scan image as the atlas. Therefore, contour fusion cannot be used to mitigate against registration errors. Furthermore, because the CBCT scan image is of a much lower quality than the 3DCT scan image, the accuracy of the registration between the 3DCT scan image and the CBCT is much lower than would be expected between CTs as in ABAS.

Consequently, it would be desirable to adopt an automated contouring approach to CBCT scan images so organs on the scan can be automatically contoured. The approach may use a machine learning model, or a model which uses an alternative automated contouring algorithm, or another alternative auto contouring approach. These approaches would require a large database of contoured CBCT scan images (CBCT atlases) from which to learn. Indeed, in the case of ML-based contouring for 3DCT scan images there are thousands of previously contoured cases from which to learn, since contouring is required for the treatment. Whereas, CBCT scan images are not contoured manually in routine practice, and therefore the data availability is very limited.

While CBCT scan images could be contoured manually to build such a database of atlases, the lower quality of CBCT scan images makes manual contouring of these scan images more difficult, more time consuming and, more importantly, highly variable. Therefore, any database of manually contoured cases would have a high inter- and intra-observer contouring variability which would reduce the quality of any created ML model.

An alternative approach would be to use deformable image registration to map contours from the patient's CT scan image to the CBCT scan image, as described previously. However, as already highlighted, such image registration is subject to errors and would result in inaccurate contours on the CBCT scan image. Consequently, the ML model learnt from a database created in such a way would be degraded by inclusion of erroneous segmentations.

Approaches and methods to training a model for auto-segmentation using supervised convolutional neural networks (CNNs) are well described in the literature (e.g. [8, 9]), but require a large database of images with known segmentation as an input.

Thus, there is need of efficient methods of automatic contouring of CBCT images, and there is need for automatic methods to build a suitable and large database of CBCT images as a prerequisite to learn a model for a machine learning-based solution.

The present invention provided a novel approach for the development of a training database of synthetically generated images to enable machine learning contouring of CBCT images.

Accordingly, the invention seeks to mitigate, alleviate or eliminate one or more of the abovementioned disadvantages singly or in any combination.

According to a first aspect of the present invention, there is provided a method of generating synthetic scan images for use in a database of image and contour pairs, where the database is used in the delineation of features in one or more real scan images, comprising the steps of: providing a delineated real scan image acquired using a first image scanner defining a model related to the generation of a synthetic scan image using a second image scanner, processing the delineated real scan image using the model to generate said synthetic scan image, and mapping contours from the delineated real image to the synthetic image to form a new synthetic image-contour pair; repeating said providing, defining and processing steps for a plurality of delineated real scan images to generate a corresponding plurality of synthetic scan images and contour pairs for the database of image and contour pairs; using said database of generated plurality of synthetic scan images and contour pairs to optimise an automated contouring algorithm, where the optimised algorithm generates contours for the real scan images of the same type as the synthetic scan images; processing one or more further real scan images of the same type as said synthetic scan images to contour and delineate features on said further real scan image using said optimised automated contouring algorithm.

Preferably, the model is derived from one or more of the operating parameters of the second image scanner used for the real-time acquisition of a second scan image. In an embodiment of the invention the model is a model that uses one of more of the following operating parameters of the second image scanner: the distance of the beam source from the isocentre of the gantry of the scanner, $D_{SO}$; the distance between the detector and the beam source of the scanner, $D_{DO}$; the distribution of detector elements on the detector array of the scanner; the energy of the beam source of the scanner; the rotational gantry position $\beta_t$ of the scanner.

In preferred embodiment of the invention, the model is a geometric model using operating parameters related to the geometric arrangement of the second image scanner. Alternatively, the model may use physical operational parameters of the second image scanner.

Preferably, processing the first delineated scan image includes modelling the first delineated scan image with the physical characteristics of the second scanner.

In an embodiment of the invention, the first delineated scan image is one of: a CT image, an MRI image, an ultrasound image. In a further preferred embodiment of the invention the first delineated scan image is a CT scan image, and the synthetic scan image is a CBCT scan image.

In a further embodiment of the invention, the first delineated CT scan image is processed by collecting 2D projections of image intensities for one or more rotational gantry positions.

In an example of the invention, the processing of one or more of said delineated scan image to generate said synthetic image is performed using a neural network.

In an example of the invention, processing of one or more of said delineated scan image and synthetic scan image is performed using Machine Learning techniques. Preferably, the Machine Learning is performed using generative adversarial networks (GANs).

Preferably, the original delineated real scan image may be transformed or deformed before the image is processed, and the method steps performed for the resultant transformed or deformed scan image to provide a synthetic scan image based on the transformed or deformed scan image. Further preferably, the transformation or deformation of the image may be at least one of rigid or non-rigid; anatomical or arbitrary, where arbitrary transformation or deformation comprises a skew or rotation transformation or deformation.

In a second embodiment of the invention there is provided an imaging system for generating synthetic scan images comprising at least one processor arranged to: store a database of image and contour pairs, where the database is used in the delineation of features in one or more real scan images, comprising the steps of: provide a delineated real scan image acquired using a first image scanner; define a model related to the generation of a synthetic scan image using a second image scanner, process the delineated real scan image using the model to generate said synthetic scan image, and mapping contours from the delineated real image to the synthetic image to form a new synthetic image-contour pair; repeat said providing, defining and processing steps for a plurality of real delineated scan images to generate a corresponding plurality of synthetic scan images and contour pairs; optimise an automated contouring algorithm using said generated plurality of synthetic scan images and contour pairs, to contour real scan images of the same type as the synthetic scan images; process one or more further real scan images of the same type as said synthetic scan images to contour and delineate features on said further real scan image using said optimised automated contouring algorithm.

These and other aspects of the invention will be apparent from and elucidated with reference to the embodiments described hereinafter.

Examples of the invention solve one or more of the aforementioned problems as described in the following description.

Examples of the invention address this need by developing a system and method for automatically contouring scan images by developing an approach to generate synthetic scan imaging data, based on real patient anatomy, for which there is already a known segmentation. In a preferred example of the invention the real scan image is a CT scan image, and the synthetic scan image is a CBCT scan image. In an example of the invention, the method uses machine learning, such as generative adversarial networks (GANs), or alternative automated contouring algorithm to contour the scan images.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION

Here we disclose an example of an efficient approach to generate a database of synthetic contoured scan images that can be used as a training database, for the delineation of features, e.g anatomical features in real scan images. The database of synthetic contoured images that is generated is may be used to train and/or optimise machine learning algorithms to generate contours for real scan images, or as an input to other automated contouring algorithms to contour real patient images.

Preferably, the synthetic scan images generated for the database are CBCT scan images, but other types of scan images may also be generated and stored as images in the database. High quality 3DCT scan images are acquired from patients and the scan images are routinely contoured as part of the radiotherapy treatment planning approach. Using this 3DCT imaging, a synthetic CBCT scan image is generated. The synthetic scan image correctly models the same anatomy of the patient scanned for the 3DCT scan image. Having developed the synthetic CBCT scan images of a patient with the same anatomy and positioning as the original 3DCT scan image (so the original and synthetic images have the same frame of reference), the existing clinical contours correspond to the same anatomy on the synthetic CBCT scan image by construction. This new synthetic imaging and segmentation on the synthetic images can therefore be used, in an example of the invention, to train a model for scan image segmentation. In an embodiment of the invention the model can be trained using machine learning. In a example of the invention, the model uses convolutional neural networks (CNNs). Alternatively, the synthetic database can be used as an input to an auto-contouring system, or for the training or development of an auto-contouring system.

Figure 3:
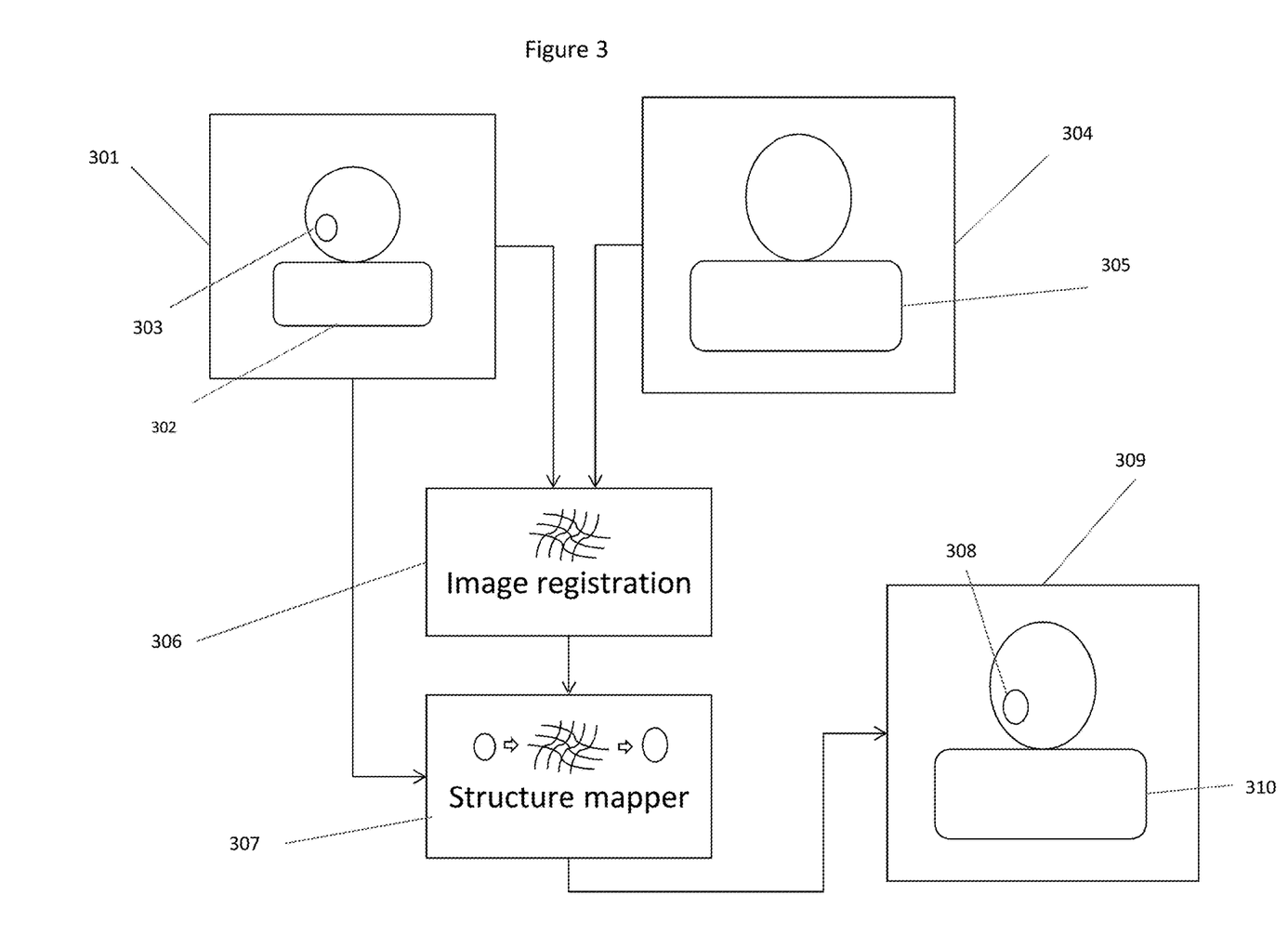
FIG. 3 shows an example of a prior art atlas-based auto-contouring system.

FIG. 3 illustrates a method of atlas-based auto contouring. An original medical scan image 301 (usually a 3DCT scan image in the context of radiotherapy, but other scan images may be provided) of a previous patient 302 with structures already contoured/marked-up 303 is aligned to a new medical scan image 304 of the current patient 305 using an image registration system 306. The patients in the two scan images are different patients. The registration system 306 calculates the spatial correspondence between the original and the new scan images. This spatial correspondence between the scan images of the different patients is used by a structure mapper 307 to transform the structure 303 from the atlas patient scan image 301 to the current patient scan image 305. The system then produces an estimated structure 308 for the current patient 310 on the scan image 309. Note in this figure 304 and 309 represent the same scan image.

Figure 4:
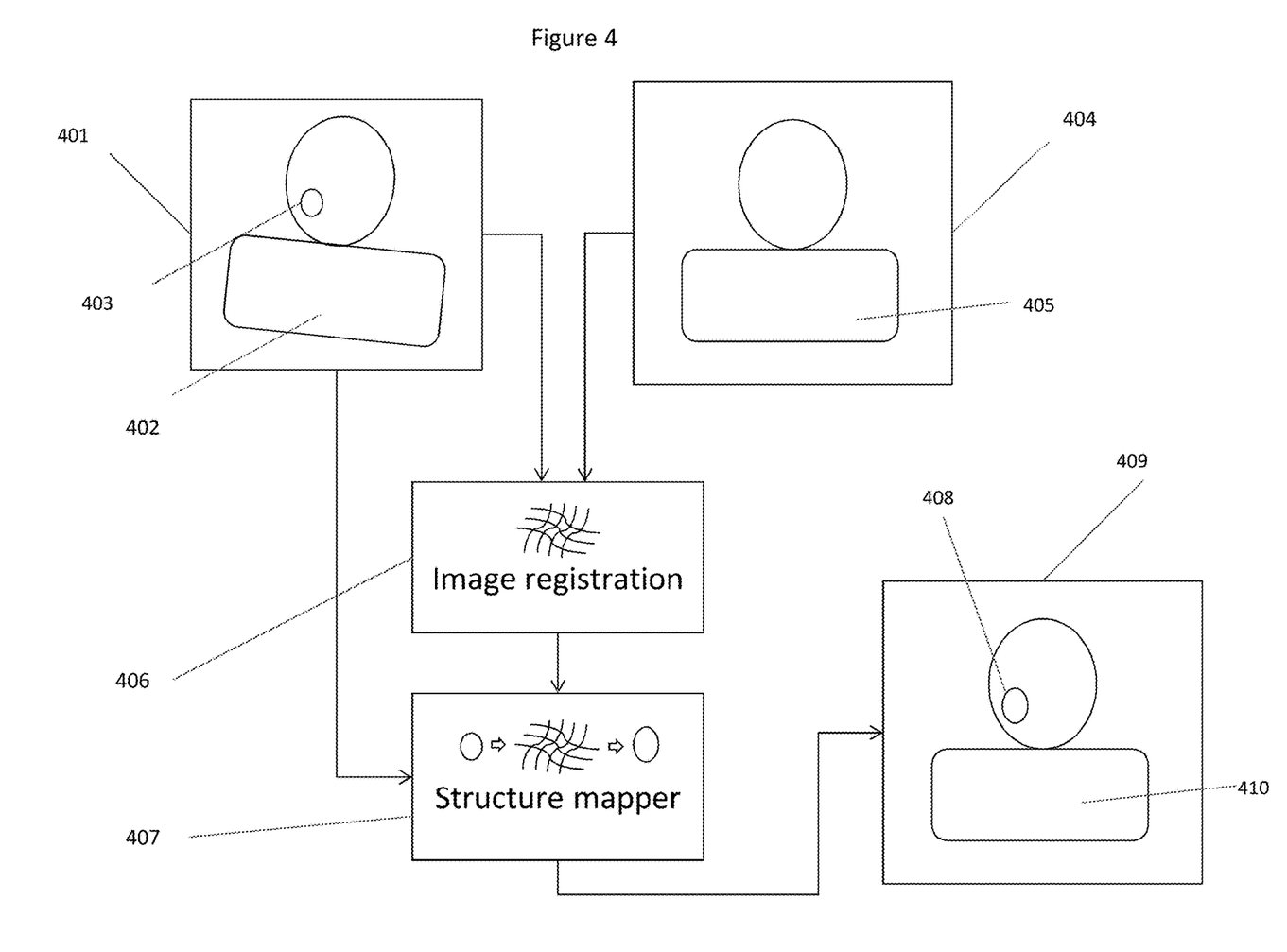
FIG. 4 illustrates an example an auto-contouring solution using images for the same patient.

FIG. 4 illustrates the method of using the original 3DCT scan image to contour the CBCT of the same patient. In this method, the 3DCT scan image and the CBCT scan image are of the same patient, whereas in FIG. 3 the 3DCT scan image and the CBCT scan image are for different patients. An original medical scan image 401, usually a 3DCT scan image in the context of radiotherapy, of a patient 402 with structures already contoured/marked-up 403 is aligned to a new medical scan image 404, in this case a CBCT scan image, of the same patient 405 using an image registration system 406. In this method as illustrated the patient may be in a different position when the CBCT scan image is obtained, compared to the patient position when the 3DCT scan image was obtained. The registration system 406 calculates the spatial correspondence between the scan images. This spatial correspondence is used by a structure mapper 407 to transform the structure 403 from the original scan image 401 to the current scan image 404. The system then produces an estimated structure 408 for the current patient on scan image 409. Note 404 and 409 represent the same scan image, while 410 is the same as 405.

In the example of FIGS. 3 and 4 the scan images 301, 304, 401, 404 are CT scan images. However, in other embodiments of the invention the images may be MRI images, ultrasound images or other types of medical scan images.

Figure 5:
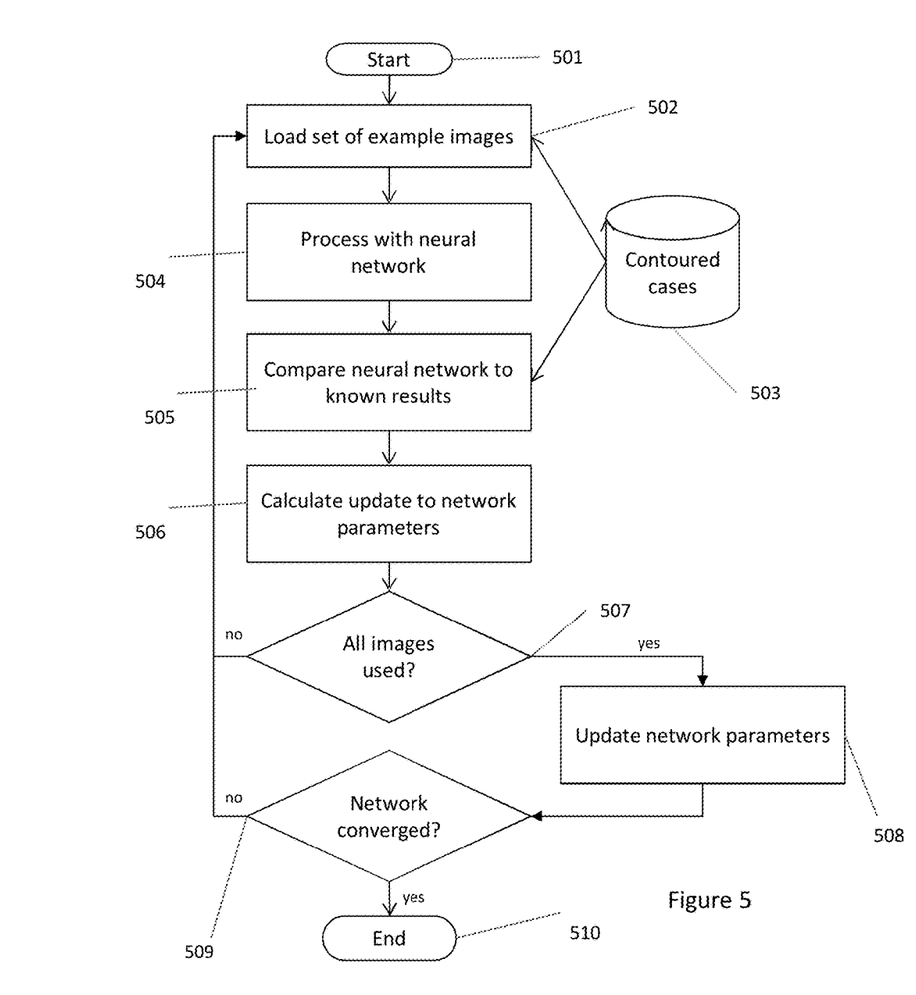
FIG. 5 is a flow diagram showing convolutional neural network contouring.

FIG. 5 illustrates an example of the process of training and using a convolutional neural network for contouring a patient scan image. As described, the contouring of the scan image is done using a convolutional neural network, but other methods for contouring of the scan image may also be used. The training process start at 501 and progresses to 502. At 502 one or more example scan images are loaded from a database 503 of previous contoured scan images. The loaded scan images are then processed at 504 with the current form of the neural network, with its current parameter settings (these settings may have been initialised randomly, or from a prior network trained on other data). The output of the current network is then compared at 505 to the known "correct" contours for that scan image, as previously loaded from database 503. An update to the network parameters is calculated at 506 so as to reduce the error between the current contour estimate of the network and the known correct contours. The process can be iterated over the whole database of scan images 503 in batches loaded at 502, progressing from 507 back to 502 until all training images have been considered. Once all scan images, or a chosen size subset of scan images, have been considered the network parameters calculated at 506 at each iteration are combined and the network is updated at 508. The process from 502 to 508 is repeated for a set number of iterations or until it is determined that the network parameters have converged at 509. Once this iteration process is complete, the training terminates at 510 with a set of network parameters tuned.

Figure 6:
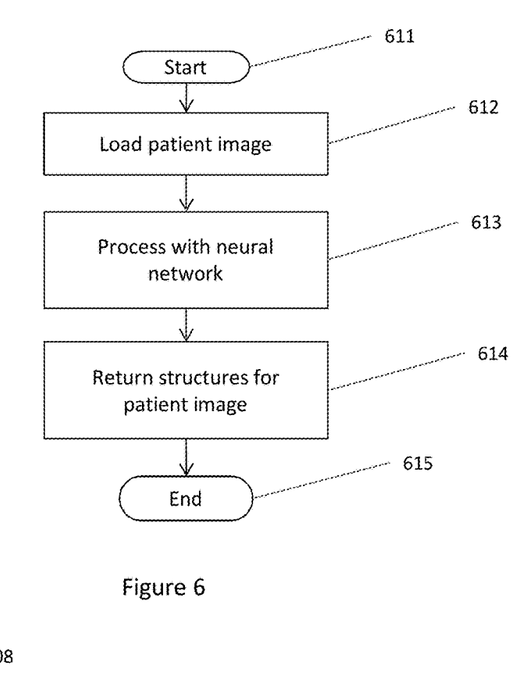
FIG. 6 is a flow diagram showing an example of contouring a patient image with a neural network.

The process to contour a new patient scan image is shown in FIG. 6. The process starts at 611, and progresses to 612. At 612 the new patient scan image is loaded into the system. This is passed to the neural network previously trained using the process 501-510, where it is processed at 613.

As described, in the example of the invention, the processing is carried out using neural networks, but the loaded scan images may be processed using other auto-contouring techniques or algorithms trained or optimised and developed using the synthetic image/contour pairs. The result of this processing is the contour(s) required. These contours are returned or saved at 614. Once this is complete the process finishes at 615.

Figure 7:
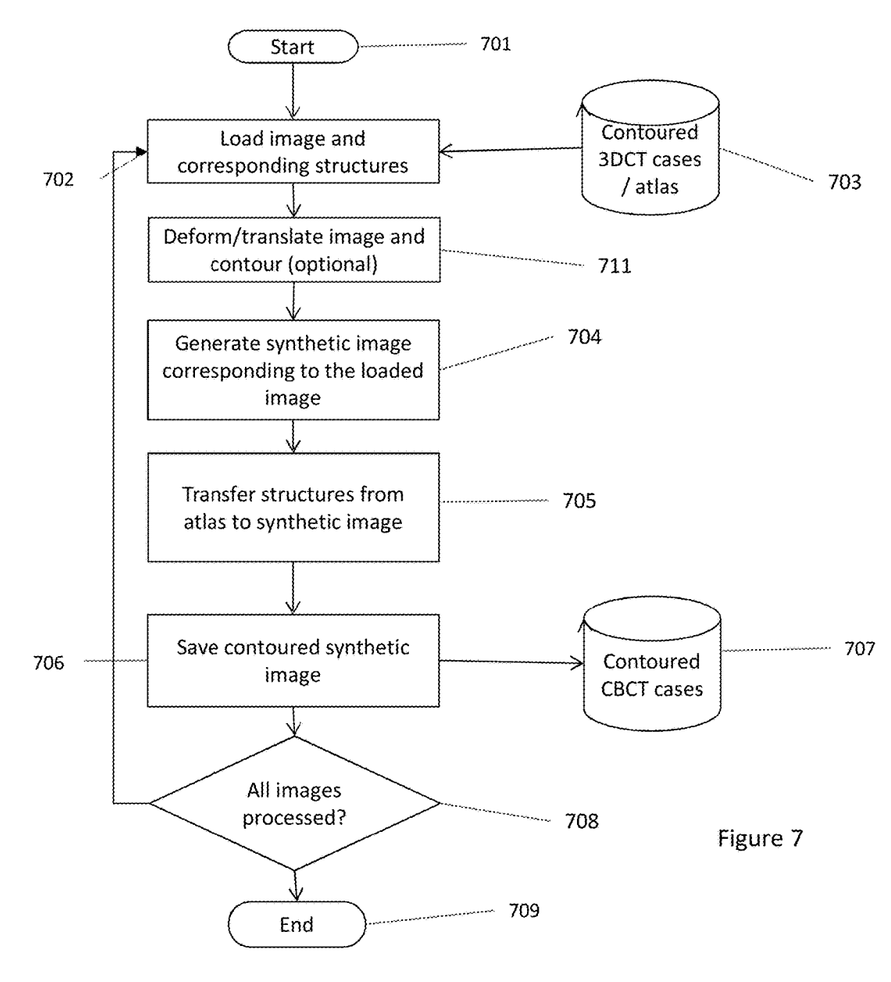
FIG. 7 is a flow diagram of a training procedure for CBCT segmentation.

FIG. 7 illustrates the process by which a database of contoured scan images can be created in an example of the invention, preferably the contoured scan images in the database will be CBCT images, but other scan image modalities may also be produced for other clinical contexts. As described the synthetic scan images are used in the database of images and contour pairs to assist in the delineation of feature in real scan images. The database may be used to optimise an automated contouring algorithm, where the optimised algorithm generates contours for the real scan images of the same type as the synthetic scan images The process starts at 701 and proceeds to 702 where a previous scan image of one modality (such as 3DCT, MRI or ultrasound), (obtained from a first image scanner with particular operating parameters) that has been previously delineated with corresponding structure contours, is loaded from database 703. The real delineated scan image is processed at 704 using a specified model, to generate a synthetic scan image of a new modality (for example, a 3DCT image is processed to produce a CBCT image). The structure contours, loaded at 702, are then mapped or transferred from the delineated real scan image at 705 to the synthetic scan image to produce a delineated synthetic scan image, created at 704. The structure contours may be copied across and duplicated in the synthetic scan, or they might be processed as part of the transfer/mapping, such as resampling the contours to the synthetic image resolution. At 706 the new synthetic scan image and corresponding contours are saved to a new database 707. At 708 the previous steps in the process (providing the delineated real scan image, defining the model, processing the real delineated image to generate the synthetic image) may be repeated until all the required data has been created, and a complete database has been populated, after which the process ends at 710. In FIG. 7, an optional step is shown at 711, between 702 and 704, whereby the real delineated scan image and corresponding contour loaded at 702 are transformed/deformed in some way, to generate a deformed or transformed image contour pair, so as to augment the data available, these steps may be performed more than once. In this way, the size of database 707 of contoured CBCT scan images may exceed the size of database 703 of contoured 3DCT scan images. The database of contoured CBCT scan images created in this way may be used in the method of FIG. 5, as the input in step 502.

Once database 707 is created, this database may be used in the process as shown in FIG. 5 to train or optimise a system to automatically contour CBCT scan images using an automated contouring algorithm. Preferably, the algorithm will be optimised to contour the scan images. Alternatively, the process shown in FIG. 7 may be used "on the fly" such that as scan images are loaded in 502, they are converted using steps 702-706, potentially including optional step 711. Therefore, the data loaded at 502 are replaced in the training process by those saved at 706.

Figure 8:
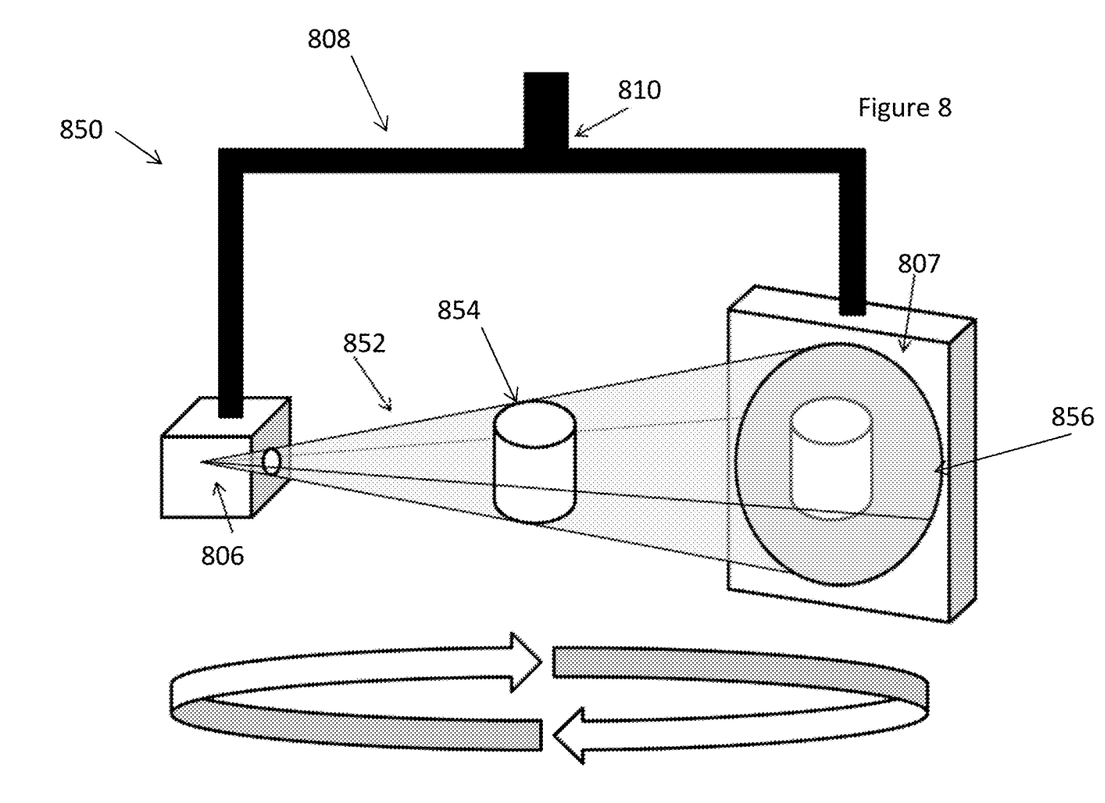
FIG. 8 is a schematic diagram of a typical CBCT scanner

FIG. 8 is a schematic of a CBCT scan imaging system 850 that can be used to generate scan images such as the CBCT scan images shown in FIG. 2. The imaging system has a gantry 808 that rotates around rotational axis 810. On one side of the gantry is the beam source 806, and directly opposite the beam source 806 is the detector array 807. The source 806 emits a conical beam 850, and the gantry is rotated around the region of interest 854 of the subject, where the region of interest is centred in the field of view for the cone beam.

Figure 9:
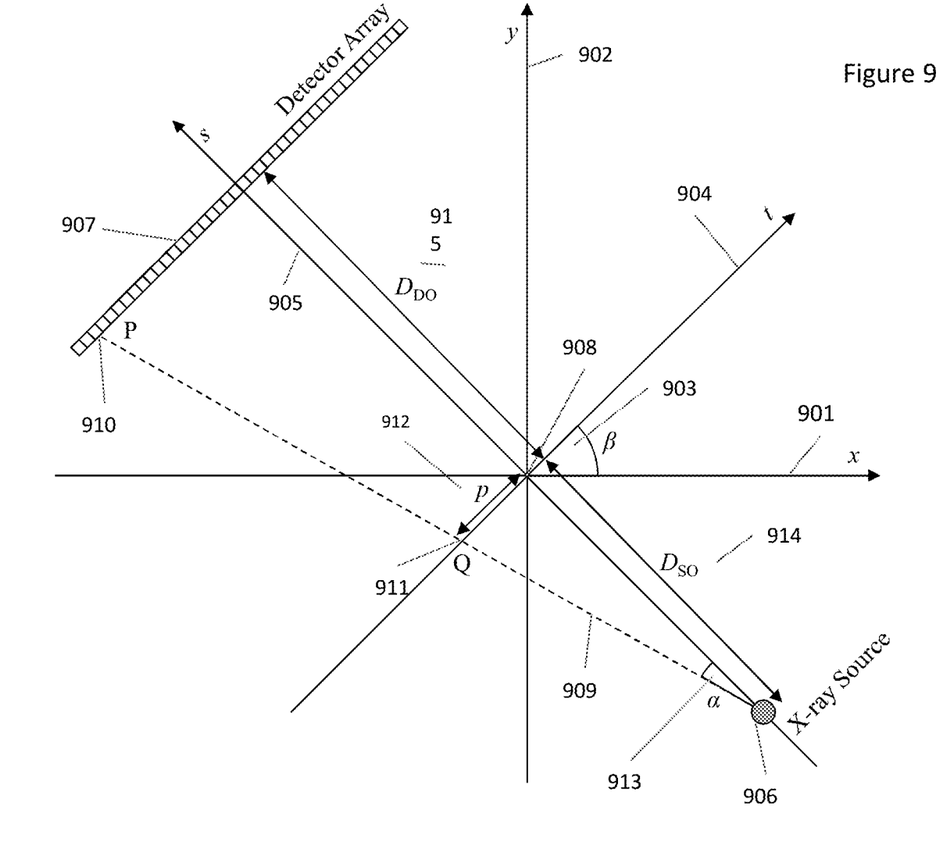
FIG. 9 is an illustration of a geometrical model used in an example of CBCT image simulation

FIG. 9 outlines a geometric model used in the CBCT simulation in an example of the invention. This is a top-down view into the rotation plane; the geometry out of the plane of rotation is not shown. The CBCT simulation requires representation of a rotating X-ray source around the subject at a given radius, (the radius may be fixed or variable) as mechanically controlled by the CBCT scanner gantry. The imaging system gantry is considered to rotate relative to global axes, x 901 and y 902. For a given rotation angle, β 903, the axes used to describe objects in the gantry's frame of reference, t 904 and s 905, are determined. This is useful since the s axis describes the central ray between the X-ray source 906, and the detector array 907 located on the opposite side of the subject to the rotation axis 908. Any given diverging straight line 909 between the source and the detector can then be parameterised for the purposes of reconstructing the CBCT data into an image. To achieve this, the point of intersection of the line with the detector panel at P 910 is projected back to its intersection the t axis at Q 911. This scales the tangential crossing of the ray along the divergence of the X-ray beam to obtain parameter p 912 in equation 1. This requires the calculation of the beam angle, α, 913 with the source-origin distance DSO 914 and the detector-origin distance DDO 915. Almost identical arguments are made to identify the vertical projection of the line with the detector array (not shown) to obtain the elevation, ζ, in equation 1.

Figure 10:
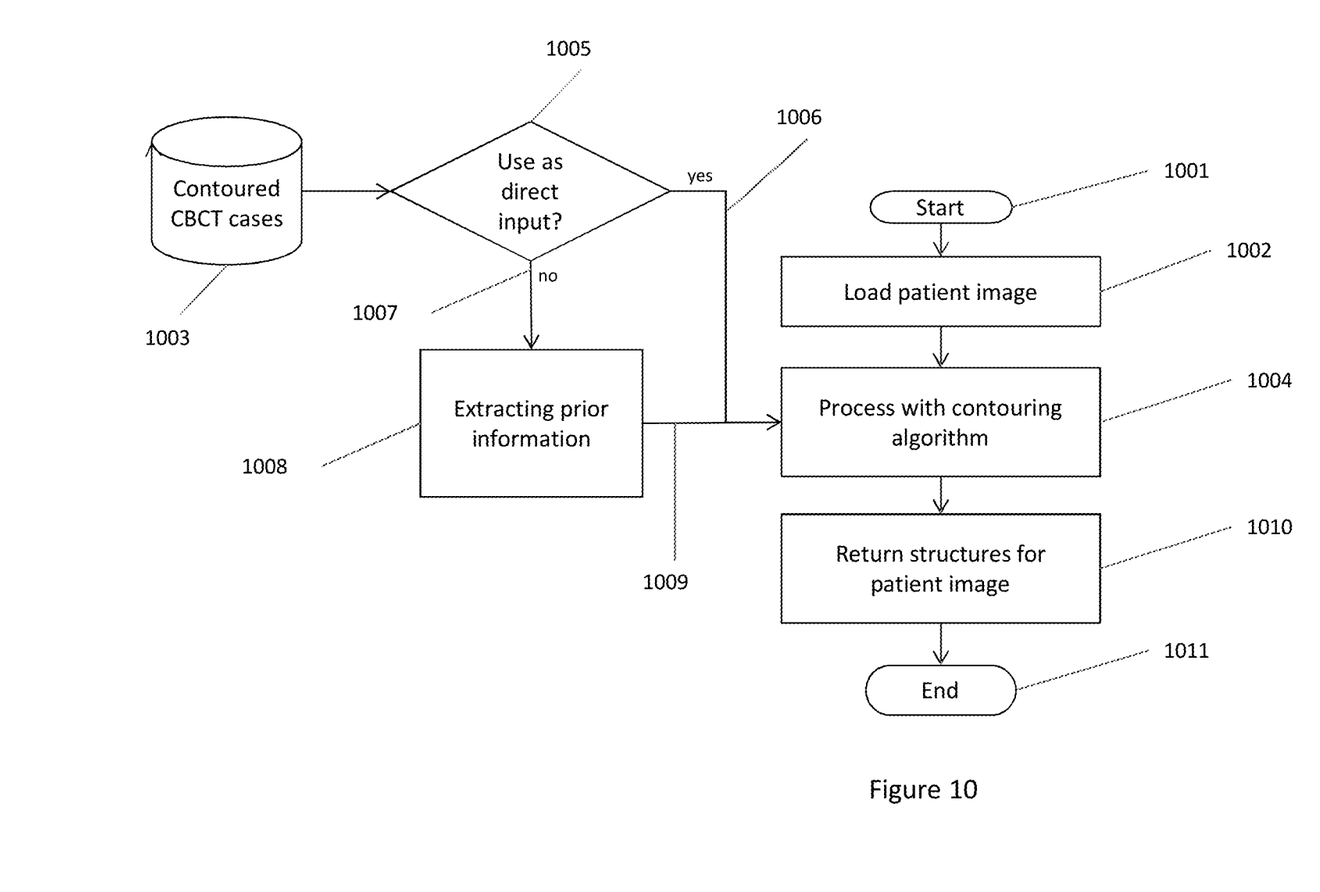
FIG. 10 is a flow diagram showing an example of an auto-contouring system that uses synthetic CBCT/contour pairs as input.

FIG. 10 illustrates a process where a database of synthetic image/contour pairs is used in a general auto-contouring system. In an example of the invention the synthetic images are CBCT scan images. The process starts at 1001, after which the patient scan image to be contoured is loaded at 1002. The application of the database, 1003, to the problem depends on the algorithm used to perform the contouring, 1004. The database images may be used directly or indirectly 1005 by the contouring algorithm. An example of a direct use is as the inputs 1006 to a multiple atlas-based auto-segmentation (M-ABAS) algorithm. Examples of indirect use 1007 are using the synthetic CBCT as test cases for parameter optimisation (e.g., fine tuning the parameters in a handcrafted algorithm), or for extracting prior information to find a shared representation (e.g., active shape models) which is then used to as part of the algorithm 1004. The algorithm is then applied to the patient image 1002 to generate structures 1010 after which the process ends at 1011.

A synthetic scan image can be generated in a number of ways in examples of the invention. In a preferred embodiment of the invention, the scan image is a CBCT scan image, but other synthetic images may also be generated. A preferred example in the method of the invention as disclosed is to use a model of the imaging acquisition system. In an example of the invention, where the synthetic image to be generated is CBCT, the model takes account of the geometry of the imaging scanner used for obtaining the CT image. In some examples of the invention the model also models the physics involved in the image creation. In a preferred embodiment of the invention the model used to generate the synthetic CBCT scan comprises the following steps:

1. Define a geometric model of the CBCT scanner 850 used to generate the target image. Important parameters include the distances of the source and the detector panel from the gantry isocentre ($D_{SO}$ and $D_{DO}$, respectively), distribution of detector elements on the panel, any panel offset from the centreline, and acquisition parameters such as number of angular steps ('views'), total arclength, and X-ray beam energy (often with a peak energy around 120 keV). These are shown in FIG. 9

2. Convert the originating 3DCT scan image from CT number (in Hounsfield units) to linear attenuation coefficient (in $mm^{-1}$), scaled to the CBCT beam energy. This allows for modelling of beam energy dependent image features.

3. Perform a simulated data acquisition: At each rotational gantry position, $\beta_i$, collect a 2D projection of the original image intensities. There are many ways to do this, for example the Siddon ray tracing algorithm [10] which calculates ray-sums of the voxel intensities along the set of divergent lines between the source position and the detector element positions. Alternatively, one can use voxel-driven, distance-driven, or slant-stacking projectors [17].

4. Physical and technical aspects of the acquisition can be used to make the simulated scan images more realistic, such as beam hardening, scatter effects, and system noise. For example, individual X-ray photons have an energy and a direction of propagation, but the beam will be comprised of many such photons. While traversing an object, they may be absorbed or deflected in a way that depends on the physical properties of the material crossed and the energy of the photon. In this case, the total flux incident upon the detector is described by the polychromatic absorption equation $$\Phi = \int_0^{E_{max}} \Phi_0(E) \exp[-\int \mu(r,E) ds] dE$$

for an initial polychromatic beam of spectral flux $\Phi_0$ traversing a material of linear attenuation coefficient μ. There are increasingly complex ways to model effects such as this, with a trade-off between accuracy and processing time.

5. The set of projections can then be pre-processed prior to reconstruction. The exact pre-processing steps depend on the applied reconstruction algorithm and the effects included in step 3. For example, one might use the FDK reconstruction algorithm [11], since it is currently the most widely-applied clinical reconstruction algorithm for CBCT data [12]. It is fast, but inexact; however, image errors generated by the algorithm would equally be expected in real clinical CBCT reconstructions where this reconstruction approach is used. In this case, the acquired projections, $R_\beta(p, \zeta)$, are pre-processed to obtain the modified projections, $$Q_\beta(p, \zeta) = \left[ \frac{D_{SO}}{\sqrt{D_{SO}^2 + \zeta^2 + p^2}} R_\beta(p, \zeta) \right] \star \frac{1}{2} h(p), \quad (1)$$

where p and ζ are the diverging-ray projected coordinates (parallel to t and z, respectively) at the origin, and h(p) is a 1D ramp filter (which may also include an apodisation filter).

6. Modified projections are then reconstructed into scan images using a back-projection algorithm. Again, there are many options to choose from for this operation; For example, a voxel-based back projector has the advantage of being fast and allows an easy application of the FDK algorithm. To achieve this, the reconstruction image array is rotated to the respective gantry position of a given projection, and the centre of each voxel is projected along the divergent cone beam lines into the projected coordinate system. This then allows sampling of that projection's contribution to the reconstructed voxel intensities via bilinear interpolation. As part of the geometric scaling and due to the facets of the FDK algorithm, some additional scaling factors are applied here. The overall FDK reconstruction of the set of modified projections, $Q_\beta(p, \zeta)$, into the gantry frame of reference (t, s, z), is $$g(t, s, z) = \int_0^{2\pi} \frac{D_{SO}^2}{(D_{SO} + s)^2} Q_\beta \left( \frac{D_{SO} t}{D_{SO} + s}, \frac{D_{SO} z}{D_{SO} + s} \right) d\beta. \quad (2)$$

For more details on the background on this reconstruction algorithm, please see [13].

Note; more complex approaches to simulating the CBCT acquisition can be performed at steps 1-4, such as using Monte Carlo modelling, or other simulation methods, to account for different beam energies and/or scatter.

Once the CBCT image has been generated, it can be used to populate a database of images and contour pairs for various purposes. For example, the database may be used for generating synthetic scan CBCT images from real CT scan images in a way that preserves the spatial correspondence between the real scan image and the synthetic image and also allows for the mapping of contours from the real CT scan images to the corresponding synthetic CBCT scan images. This database of delineated CBCT scan images can then be used to, e.g., train a machine learning algorithm (such as a convolutional neural network) for the task of optimising an auto-contouring algorithm that generates contours which will be used to auto-contour real CBCT scan images. Alternatively, in a further embodiment of the invention the database could be used to optimise the parameters in a hand-crafted auto-contouring algorithm. In general, such a database of synthetic scan images and contour pairs would be useful for any task where relatively little extant data are available for a task (such as expertly contoured CBCT images) but similar related data exist (such as expertly contoured CT images) in a way that the prior knowledge for the task can be transferred to create a surrogate dataset in lieu of the real one.

Alternative approaches that may be considered in other examples of the invention include the use of machine learning methods to generate synthetic scan images, such as synthetic CBCT scan images from the real 3DCT scan image, in the same manner as [14]. However, such an approach has the limitation that co-aligned 3DCT and CBCT scan images are required to correctly learn how to generate the synthetic scan image from the original one. This process of alignment would use deformable image registration, and be subject to the potential accuracy drawback already identified for using the deformable image registration to directly map the contours between the images. The alternative approach for synthetic image generation using a type of generative adversarial networks (GANs) for the Machine Learning. An example of this is proposed in [15] for generating synthetic CT scan images from MR with a cyclical GAN. In such an approach a synthetic CBCT scan image would be generated from a CT scan image and at the same time a synthetic CT scan image is generated from CBCT scan image, such that the use of both networks in a cycle should generate the original scan image. A discriminator network is used to confirm that synthetic scan images looks plausible. This approach allows for training with unpaired (un-aligned scan images). However, while it is likely that the synthetic scan image has the same frame of reference as the original scan image (empirically they appear similar in the paper), there is no explicit correspondence required in the proposed method (and no theoretical demonstration provided in the paper), thus the contours may not accurately map between the original CT scan image and synthetic CBCT scan image. This limitation is highlighted in [16], where it is demonstrated that anatomical features can be created or lost.

Furthermore, it is noted that while this GAN-based approach does not require paired data, it still requires a substantial number of examples of data from both modalities. A further advantage of the physical simulation of CBCT scan images from 3DCT scan images is the ability to develop a solution for any particular acquisition device without the requirement to accumulate data for that device. Thus, it would be possible to generate data for training a ML auto-contouring model to be used clinically to segment scan images of patients acquired using a new CBCT image device before even acquiring a single CBCT scan image of patient on that device. All is needed is the physical model of the acquisition process. For example, if an institution decided to change the acquisition parameters of the on-board imaging device (to comply for example to a change of regulation regarding dose limits), the institution would be able to plan ahead for this change by simulating the needed data for training the auto contouring solution with the new parameters. Thus, the institution would be able to continue auto contouring as soon as the new protocols are in place, without needing to acquire any imaging for the purpose of training the auto contouring solution.

A further advantage of this invention relates to data augmentation. A common approach to augment the size of a dataset used for training of a CNN is to generate additional data by performing transformations to both the original imaging and to the corresponding segmentations. However, CBCT has a number of strong imaging artefacts related to patient position relative to the scanner gantry. Physical differences in the acquisition lead to an increased fraction of scattered photons, for example, leading to contrast reduction, reduced CT number accuracy, and streaks [18]. Additional technical problems such CBCT's inability to meet the Tuy-Smith data sufficiency condition, and the fact that common clinical practice opts for fast, rather than exact, reconstruction algorithms, give rise to data truncation, shape distortion, and intensity drops [19]. Thus, performing transformations directly on the CBCT scan images would produce additional data (more scan images) with un-representative artefacts, thus reducing the quality of the training dataset, and therefore the trained model. To overcome this limitation, we disclose that the original 3DCT imaging set can be subject to data augmentation (transformation, deformation, addition of noise etc) to generate additional imaging/segmentation pairs of realistic 3DCT scan images. The transformation or deformation of the images may include rigid or non-rigid deformation, anatomical transformation or deformation such as skew or rotation, or other arbitrary transformation or deformation. These additional 3DCT imaging/segmentation pairs can subsequently be used as the input to the synthetic CBCT imaging/segmentation pairs. In this way, data augmentation can be performed while generating images with physically-realistic imaging artefacts.

Novel features of this invention include the generation of synthetic CBCT scan images using modelling to derive contoured CBCT data as an input to train a machine learning system for contouring CBCT scan images. They also include the generation of synthetic CBCT scan images using modelling to derive contoured CBCT data as an input to train a CNN for contouring CBCT, as well as the use of physical modelling to generate a synthetic CBCT as an input to train a CNN for contouring CBCT and the use of machine learning for contouring CBCT.

Preferred technical features of examples of the invention include the generation of synthetic CBCT with anatomical correspondence to a known CT to derive contoured CBCT data as an input to train a CNN.

Advantages of Invention include the generation of a database of images and segmentations with accurate mark-up and realistic imaging artefacts. Further advantages include the efficient auto-contouring of CBCT to aid adaptive radiotherapy decision support.

Preferred examples of the invention can use physical modelling to generate the synthetic CBCT scan image from a known CT scan image. Examples of the invention may also use GAN to generate the synthetic CBCT scan image from a known CT scan image. Further examples of the invention may use data augmentation on the known CT database prior to generation of synthetic imaging for the purpose of training a CNN.

Examples of this invention may be applied to any or all of the following: Picture archiving and communication systems (PACS); Advanced visualisation workstations; Imaging Acquisition Workstations; Web-based or cloud-based medical information and image systems; Radiotherapy Treatment planning system (TPS); Radiotherapy linear accelerator consoles; Radiotherapy proton beam console.

The present invention has been described with reference to the accompanying drawings. However, it will be appreciated that the present invention is not limited to the specific examples herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system. Therefore, some examples describe a non-transitory computer program product having executable program code stored therein for automated contouring of cone-beam CT images.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system. The tangible and non-transitory computer readable media may include, for example and without limitation, any number of the following: magnetic storage media including disk and tape storage media; optical storage media such as compact disk media (e.g., CD-ROM, CD-R, etc.) and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims and that the claims are not limited to the specific examples described above.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an,' as used herein, are defined as one or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an.' The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

REFERENCES

[1] Sharp G, Fritscher K D, Pekar V, Peroni M, Shusharina N, Veeraraghavan H, Yang J. Vision 20/20: perspectives on automated image segmentation for radiotherapy. Medical physics. 2014; 41(5).
[2] Schipaanboord B et al. Can atlas-based auto-segmentation ever be perfect? Insights from Extreme Value Theory. IEEE transactions on medical imaging. 2018 Jul. 16.
[3] Lustberg T, van Soest J, Gooding M, Peressutti D, Aljabar P, van der Stoep J, van Elmpt W, Dekker A. Clinical evaluation of atlas and deep learning based automatic contouring for lung cancer. Radiotherapy and Oncology. 2018 Feb. 1; 126(2):312-7.
[4] Gooding M, et al. PV-0531: Multi-centre evaluation of atlas-based and deep learning contouring using a modified Turing Test. Radiotherapy and Oncology. 2018; 127: S282-3.
[5] Brouwer C L, Steenbakkers R J, Langendijk J A, Sijtsema N M. Identifying patients who may benefit from adaptive radiotherapy: Does the literature on anatomic and dosimetric changes in head and neck organs at risk during radiotherapy provide information to help?. Radiotherapy and Oncology. 2015; 115(3):285-94.
[6] Vickress J R, Battista J, Barnett R, Yartsev S. Online daily assessment of dose change in head and neck radiotherapy without dose-recalculation. Journal of Applied Clinical Medical Physics. 2018; 19(5):659-65.
[7] Li X, Zhang Y, Shi Y, Wu S, Xiao Y, Gu X, Zhen X, Zhou L. Comprehensive evaluation of ten deformable image registration algorithms for contour propagation between CT and cone-beam CT images in adaptive head & neck radiotherapy. PloS one. 2017; 12(4):e0175906
[8] Ronneberger O et al. U-net: Convolutional networks for biomedical image segmentation. International Conference on Medical image computing and computer-assisted intervention 2015; 234-241. Springer, Cham.
[9] Nikolov S et al. Deep learning to achieve clinically applicable segmentation of head and neck anatomy for radiotherapy. arXiv preprint arXiv:1809.04430. 2018 Sep. 12
[10] Siddon R L, Fast Calculation of the Exact Radiological Path for a Three-Dimensional CT Array. Medical Physics, 12(2), 252-255. 1985
[11] Feldkamp L A et al. Practical cone-beam algorithm. Journal of the Optical Society of America A, 1(6), 612. 1984
[12] Pauwels R et al. Technical aspects of dental CBCT: state of the art. Dentomaxillofacial Radiology, 44(1), 2015.
[13] Kak A C & Slaney M, Principles of Computerized Tomographic Imaging. Classicas in Applied Mathematics 33, Society for Industrial and Applied Mathematics. 2001
[14] Han X. MR-based synthetic CT generation using a deep convolutional neural network method. Medical physics. 2017; 44(4):1408-19.
[15] Wolterink J. M et al. Deep MR to CT synthesis using unpaired data. In International Workshop on Simulation and Synthesis in Medical Imaging 2017; 14-23. Springer, Cham.
[16] Cohen J P, Luck M, Honari S. Distribution Matching Losses Can Hallucinate Features in Medical Image Translation. arXiv preprint arXiv:1805.08841. 2018 May 22
[17] Arcadu, F, et al., On the Crucial Impact of the Coupling Projector-Backprojector in Iterative Tomographic Reconstruction, arXiv ePrint arXiv:1612.05515v1, 2016 Dec. 16
[18] Rührnschopf, E. and Klingenbeck, K., A General Framework and Review of Scatter Correction Methods in X-Ray Cone-Beam Computerized Tomography. Part 1: Scatter Compensation Approaches, Medical Physics, 36(7):4296-4311, 2011
[19] Tang, X., et al., On the Data Acquisition, Image Reconstruction, Cone Beam Artifacts, and their Suppression in Axial MDCT and CBCT—A Review, Medical Physics, 45(9):761-782, 2018
[20] Srinivasan, K., et al., Applications of Linac-Mounted Kilovoltage Cone-Beam Computed Tomography in Modern Radiation Therapy: A Review, Polish Journal of Radiology, 79:181-193, 2014

We claim:

1. A method of generating synthetic scan images for use in a database of image and contour pairs, where the database is used in the delineation of features in one or more real scan images, comprising the steps of:
providing a delineated real scan image acquired using a first image scanner
defining a model related to the generation of a synthetic scan image using a second image scanner,
processing the delineated real scan image using the model to generate said synthetic scan image, and
mapping contours from the delineated real image to the synthetic image to form a new synthetic image-contour pair;

repeating said providing, defining and processing steps for a plurality of delineated real scan images to generate a corresponding plurality of synthetic scan images and contour pairs for the database of image and contour pairs;

using said database of generated plurality of synthetic scan images and contour pairs to optimise an automated contouring algorithm, where the optimised algorithm generates contours for the real scan images of the same type as the synthetic scan images;

processing one or more further real scan images of the same type as said synthetic scan images to contour and delineate features on said further real scan image using said optimised automated contouring algorithm.

2. A method according to claim 1, wherein said model is derived from one or more of the operating parameters of the second image scanner used for the real-time acquisition of a second scan image.

3. A method according to claim 2, wherein said model is a model that uses one of more of the following operating parameters of the second image scanner: the distance of the beam source from the isocentre of the gantry of the scanner, $D_{SO}$; the distance between the detector and the beam source of the scanner, $D_{DO}$; the distribution of detector elements on the detector array of the scanner; the energy of the beam source of the scanner; the rotational gantry position $\beta_i$ of the scanner.

4. A method according to claim 3, wherein the model is a geometric model using operating parameters related to the geometric arrangement of the second image scanner.

5. A method according to claim 3, wherein the model uses physical operational parameters of the second image scanner.

6. A method according to claim 5, wherein processing the first delineated scan image includes modelling the first delineated scan image with one of more of the physical operational parameters of the second image scanner.

7. A method according to claim 1, wherein the first delineated scan image is one of: a CT image, an MRI image, an ultrasound image.

8. A method according to claim 7, wherein said first delineated scan image is a CT scan image, and the synthetic scan image is a CBCT scan image.

9. A method according to claim 8, wherein the first delineated CT scan image is processed by collecting 2D projections of image intensities for one or more rotational gantry positions.

10. A method according to claim 1, wherein the processing of one or more of said delineated scan image to generate said synthetic image is performed using a neural network.

11. A method according to claim 1, wherein said processing of one or more of said delineated scan image and synthetic scan image is at least partly performed using Machine Learning techniques.

12. A method according to claim 11, wherein the machine learning is performed using generative adversarial networks (GANs).

13. A method according to claim 1, wherein the original delineated real scan image may be transformed or deformed before the image is processed, and the method steps performed for the resultant transformed or deformed scan image to provide a synthetic scan image based on the transformed or deformed scan image.

14. A method according to claim 13, wherein the transformation or deformation of the image may be at least one of rigid or non-rigid; anatomical or arbitrary, where arbitrary transformation or deformation comprises a skew or rotation transformation or deformation.

15. An imaging system for generating synthetic scan images comprising at least one processor arranged to:

store a database of image and contour pairs, where the database is used in the delineation of features in one or more real scan images, comprising the steps of: provide a delineated real scan image acquired using a first image scanner define a model related to the generation of a synthetic scan image using a second image scanner, process the delineated real scan image using the model to generate said synthetic scan image, and mapping contours from the delineated real image to the synthetic image to form a new synthetic image-contour pair;

repeat said providing, defining and processing steps for a plurality of real delineated scan images to generate a corresponding plurality of synthetic scan images and contour pairs;

using said generated plurality of synthetic scan images and contour pairs optimising an automated contouring algorithm to generate contours for real scan images of the same type as the synthetic scan images;

process one or more further real scan images of the same type as said synthetic scan images to contour and delineate features on said further real scan image using said optimised automated contouring algorithm.

* * * * *